(12) United States Patent
Eenschooten et al.

(10) Patent No.: US 8,071,757 B2
(45) Date of Patent: Dec. 6, 2011

(54) ARYL/ALKYL VINYL SULFONE HYALURONIC ACID DERIVATIVES

(75) Inventors: Corinne Eenschooten, Vanlose (DK); Morten Würtz Christensen, Lyngby (DK)

(73) Assignee: Novozymes Biopharma DK A/S, Bagsvaerd (DK)

( * ) Notice: Subject to any disclaimer, the term of this patent is extended or adjusted under 35 U.S.C. 154(b) by 733 days.

(21) Appl. No.: 12/161,717

(22) PCT Filed: Mar. 2, 2007

(86) PCT No.: PCT/DK2007/000108
§ 371 (c)(1),
(2), (4) Date: Sep. 22, 2008

(87) PCT Pub. No.: WO2007/098770
PCT Pub. Date: Sep. 7, 2007

(65) Prior Publication Data
US 2011/0257123 A1    Oct. 20, 2011

Related U.S. Application Data

(60) Provisional application No. 60/782,144, filed on Mar. 13, 2006.

(30) Foreign Application Priority Data

Mar. 2, 2006 (DK) ................................ 2006 00305
Mar. 3, 2006 (DK) ................................ 2006 00312

(51) Int. Cl.
*A61K 31/728* (2006.01)
*C08B 37/00* (2006.01)
(52) U.S. Cl. ........................................ 536/55.1; 514/54
(58) Field of Classification Search ........................ None
See application file for complete search history.

(56) References Cited

U.S. PATENT DOCUMENTS 5,128,326 A    7/1992  Balazs et al.
6,441,207 B1   8/2002  Wynberg et al.

FOREIGN PATENT DOCUMENTS

WO    WO 2005/066215    7/2005

OTHER PUBLICATIONS

Hahn et al., "Anti-inflammatory drug delivery from hyaluronic acid hydrogels" J. Biomater. Sci. Polymer Edn, (2004) vol. 15 No. 9, pp. 1111-1119.*
Laurent et al. The Faseb Journal, vol. 6, pp. 2397-2404 (1992).
Toole, Cell Biology of the Extracellular Matrix, pp. 305-341 (1991).

* cited by examiner

*Primary Examiner* — Eric S Olson
(74) *Attorney, Agent, or Firm* — Elias Lambiris

(57) ABSTRACT

A hyaluronic acid derivative, and methods of producing and using said derivative, the derivative comprising n repeating units and having the general structural formula (I), wherein, in at least one repeating unit, one or more of R1, R2, R3, R4 comprises an etherbound aryl/alkyl sulfone having the general structural formula (II), wherein R comprises an alkyl- or aryl-group, and otherwise R1, R2, R3, R4 are hydroxyl groups, OH.

19 Claims, 6 Drawing Sheets

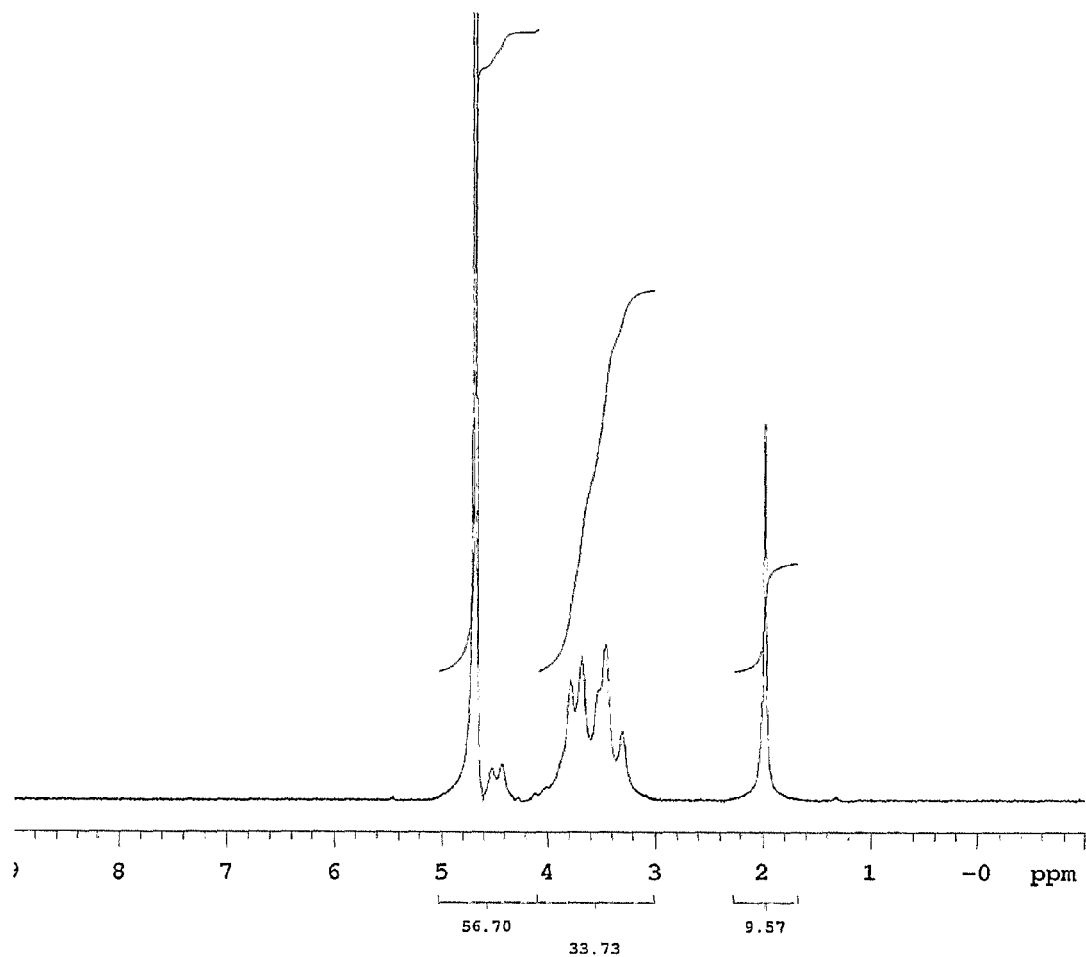
Figure 1: $^1$H NMR spectrum (HA, 300 kDa)

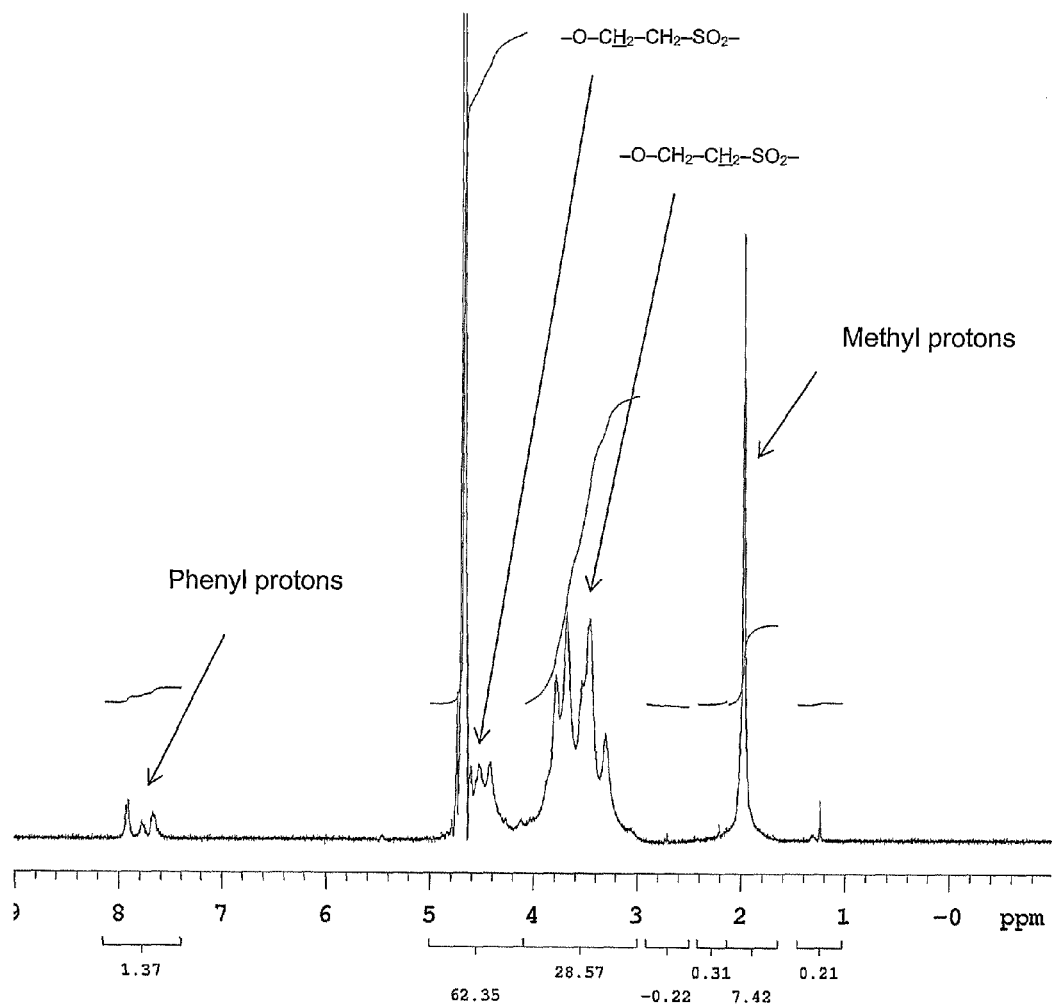
Figure 2: $^1$H NMR spectrum (PVS-HA from HA 300 kDa) PVS:HA ratio 1.5:1

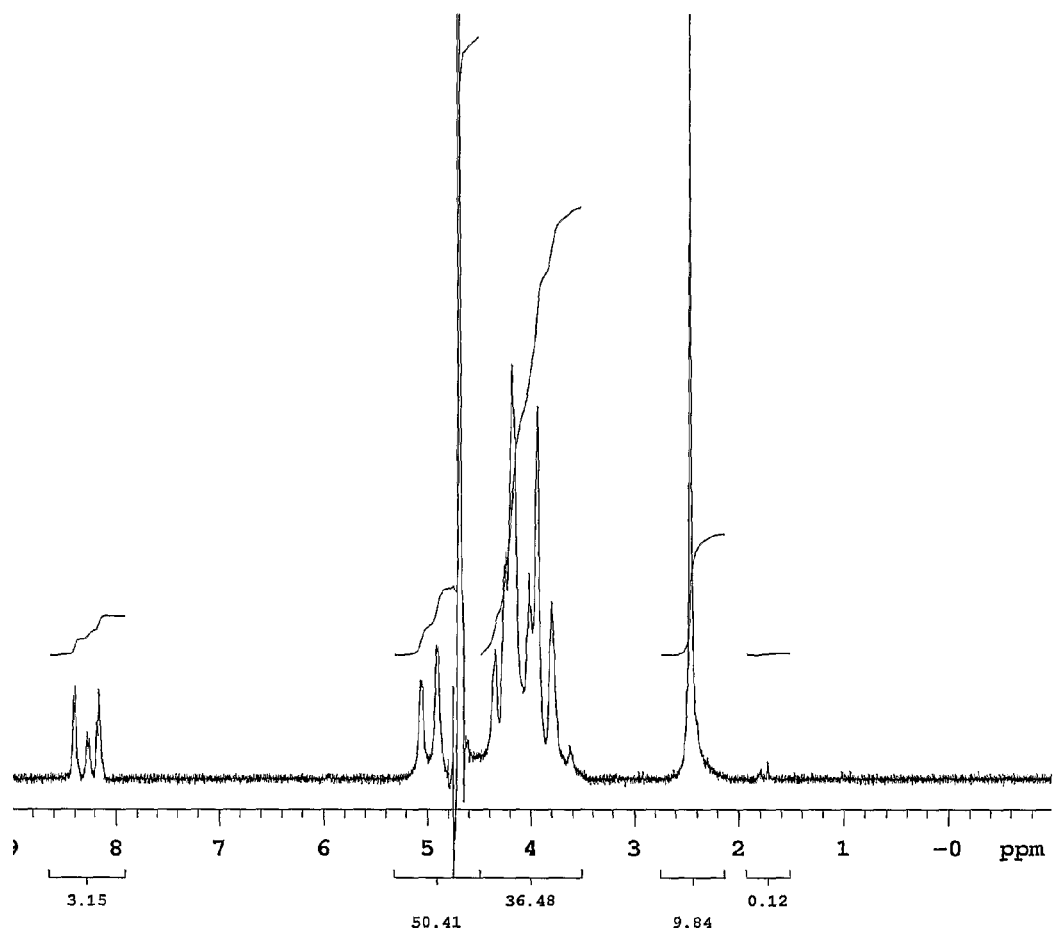
Figure 3: ¹H NMR spectrum (PVS-HA from HA 300 kDa) PVS:HA ratio 5:1

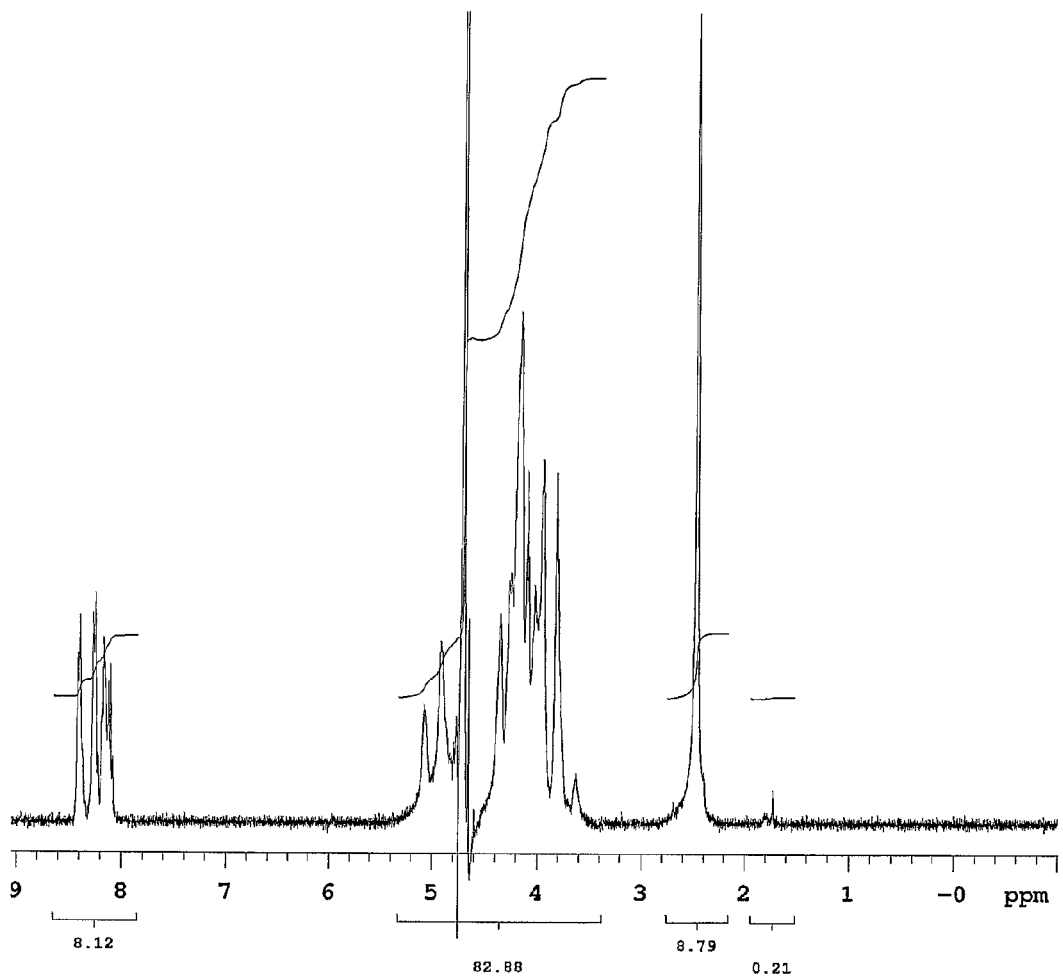
Figure 4: ¹H NMR spectrum (PVS-HA from HA 300 kDa) PVS:HA ratio 10:1

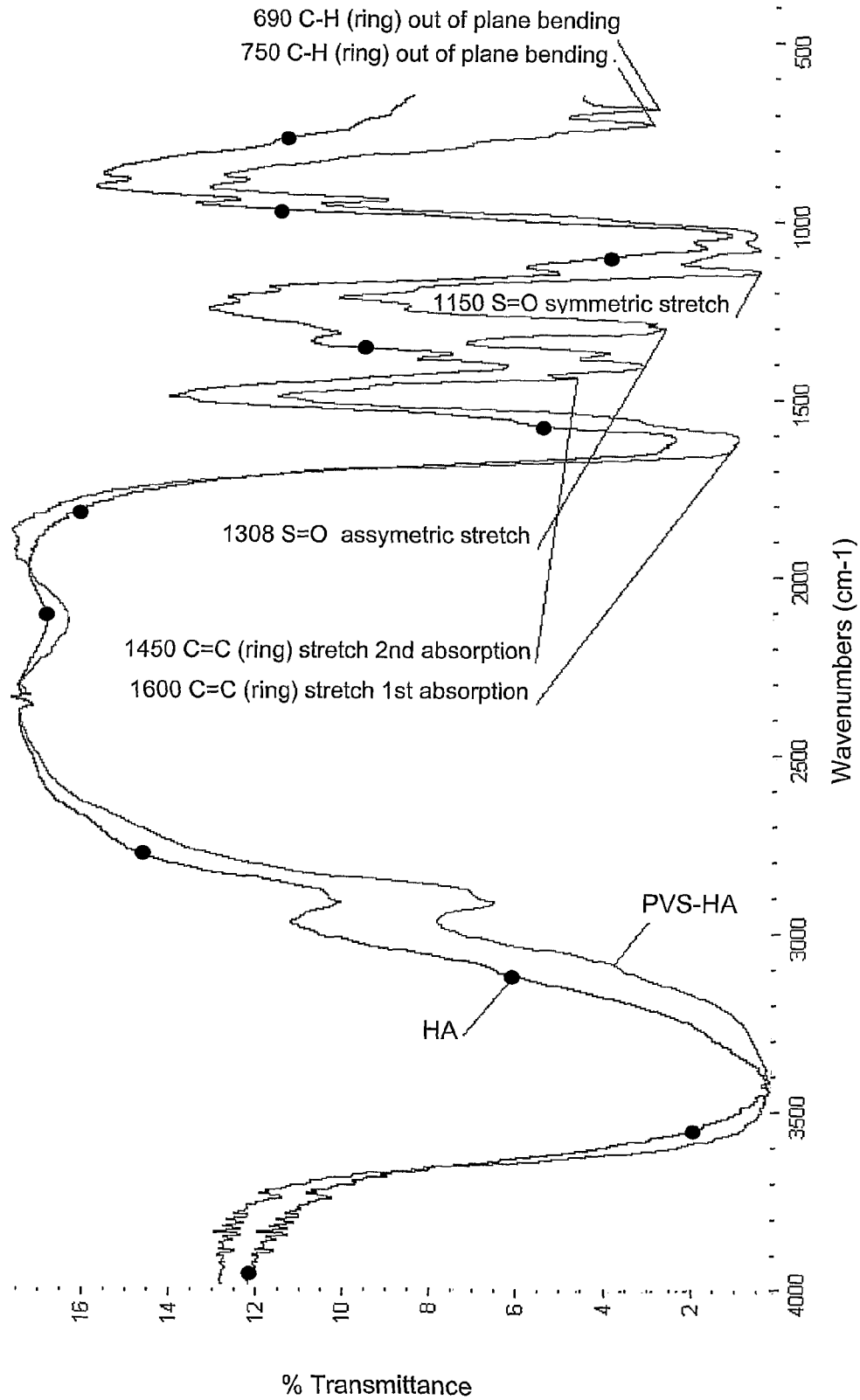
Figure 5: IR spectrum (PVS-HA from HA 300 kDa) PVS:HA ratio 10:1

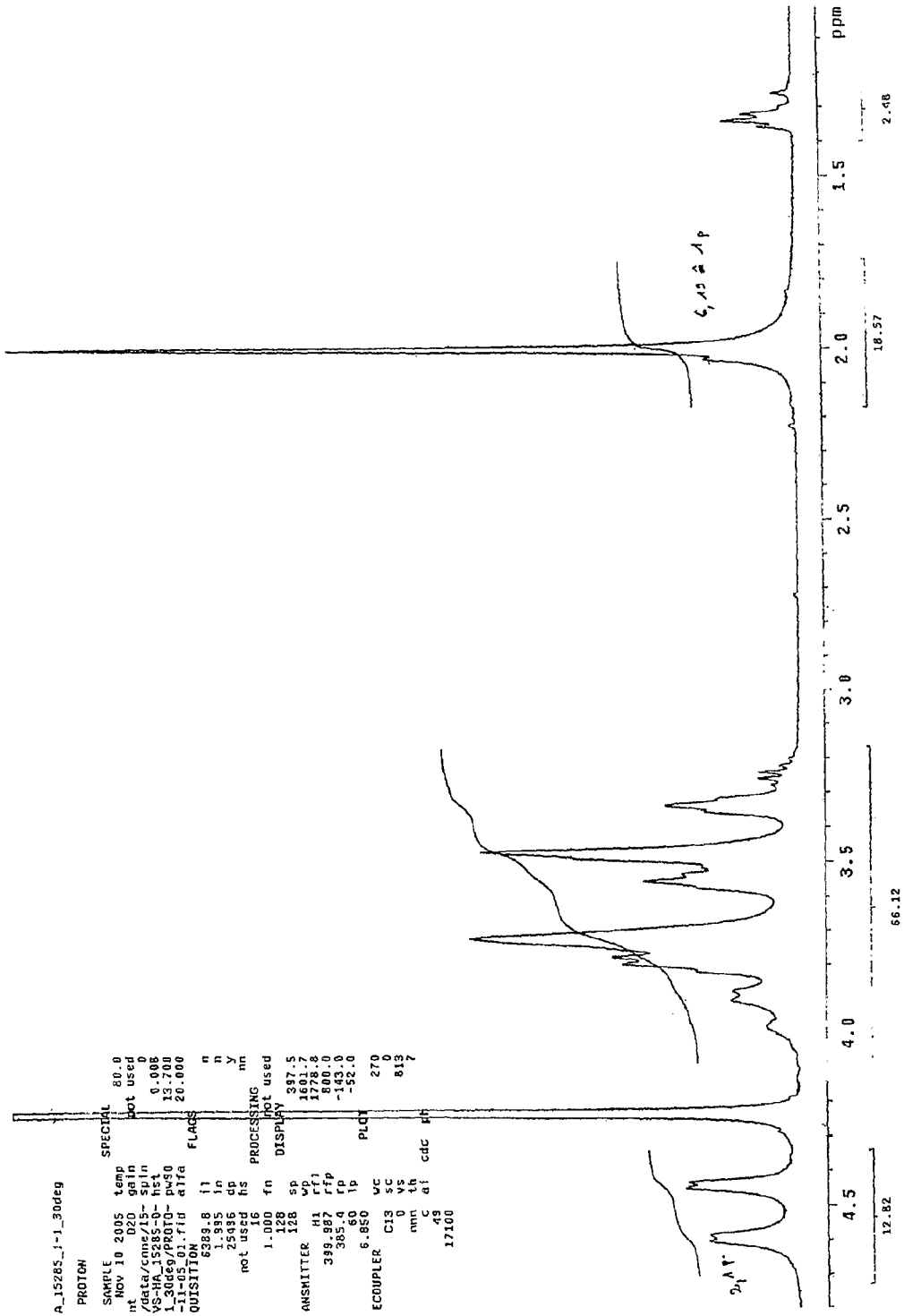
Figure 6: ¹H NMR spectrum (EVS-HA from HA 300 kDa) EVS:HA ratio 1.5:1

ARYL/ALKYL VINYL SULFONE HYALURONIC ACID DERIVATIVES

CROSS-REFERENCE TO RELATED APPLICATIONS

This application is a 35 U.S.C. 371 national application of PCT/DK2007/000108 filed Mar. 2, 2007, which claims priority or the benefit under 35 U.S.C. 119 of Danish application nos. PA 2006 00305 and PA 2006 00312 filed Mar. 2, 2006 and Mar. 3, 2006, respectively, and U.S. provisional application No. 60/782,144 filed Mar. 13, 2006, the contents of which are fully incorporated herein by reference.

FIELD OF THE INVENTION

The present invention relates to the modification of hyaluronic acid (HA) with aryl- or alkyl-vinyl sulfones to produce aryl/alkyl vinyl sulfone HA derivatives (AVS-HA), to the AVS-HA derivatives as such, to their manufacture, and to their applications and uses, particularly in the cosmetics and biomedical industries.

BACKGROUND OF THE INVENTION

The most abundant heteropolysaccharides of the body are the glycosaminoglycans. Glycosaminoglycans are unbranched carbohydrate polymers, consisting of repeating disaccharide units (only keratan sulphate is branched in the core region of the carbohydrate). The disaccharide units generally comprise, as a first saccharide unit, one of two modified sugars—N-acetylgalactosamine (GalNAc) or N-acetylglucosamine (GlcNAc). The second unit is usually an uronic acid, such as glucuronic acid (GlcUA) or iduronate.

Glycosaminoglycans are negatively charged molecules, and have an extended conformation that imparts high viscosity when in solution. Glycosaminoglycans are located primarily on the surface of cells or in the extracellular matrix. Glycosaminoglycans also have low compressibility in solution and, as a result, are ideal as a physiological lubricating fluid, e.g., joints. The rigidity of glycosaminoglycans provides structural integrity to cells and provides passageways between cells, allowing for cell migration. The glycosaminoglycans of highest physiological importance are hyaluronan, chondroitin sulfate, heparin, heparan sulfate, dermatan sulfate, and keratan sulfate. Most glycosaminoglycans bind covalently to a proteoglycan core protein through specific oligosaccharide structures. Hyaluronan forms large aggregates with certain proteoglycans, but is an exception as free carbohydrate chains form non-covalent complexes with proteoglycans.

Numerous roles of hyaluronan in the body have been identified (see, Laurent T. C. and Fraser J. R. E., 1992, FASEB J. 6: 2397-2404; and Toole B. P., 1991, "Proteoglycans and hyaluronan in morphogenesis and differentiation." In: Cell Biology of the Extracellular Matrix, pp. 305-341, Hay E. D., ed., Plenum, N.Y.). Hyaluronan is present in hyaline cartilage, synovial joint fluid, and skin tissue, both dermis and epidermis. Hyaluronan is also suspected of having a role in numerous physiological functions, such as adhesion, development, cell motility, cancer, angiogenesis, and wound healing. Due to the unique physical and biological properties of hyaluronan, it is employed in eye and joint surgery and is being evaluated in other medical procedures.

The terms "hyaluronan" or "hyaluronic acid" are used in literature to mean acidic polysaccharides with different molecular weights constituted by residues of D-glucuronic and N-acetyl-D-glucosamine acids, which occur naturally in cell surfaces, in the basic extracellular substances of the connective tissue of vertebrates, in the synovial fluid of the joints, in the endobulbar fluid of the eye, in human umbilical cord tissue and in cocks' combs.

The term "hyaluronic acid" is in fact usually used as meaning a whole series of polysaccharides with alternating residues of D-glucuronic and N-acetyl-D-glucosamine acids with varying molecular weights or even the degraded fractions of the same, and it would therefore seem more correct to use the plural term of "hyaluronic acids". The singular term will, however, be used all the same in this description; in addition, the abbreviation "HA" will frequently be used in place of this collective term.

HA plays an important role in the biological organism as a mechanical support for the cells of many tissues, such as the skin, tendons, muscles and cartilage, it is a main component of the intercellular matrix. HA also plays other important parts in the biological processes, such as the moistening of tissues, and lubrication.

HA may be extracted from the above mentioned natural tissues, although today it is preferred to prepare it by microbiological methods to minimize the potential risk of transferring infectious agents, and to increase product uniformity, quality and availability.

HA and its various molecular size fractions and the respective salts thereof have been used as medicaments, especially in treatment of arthropathies, as an auxiliary and/or substitute agent for natural organs and tissues, especially in ophtalmology and cosmetic surgery, and as agents in cosmetic preparations. Products of hyaluronan have also been developed for use in orthopaedics, rheumatology, and dermatology.

HA may also be used as an additive for various polymeric materials used for sanitary and surgical articles, such as polyurethanes, polyesters etc. with the effect of rendering these materials biocompatible.

SUMMARY OF THE INVENTION

The invention is related to the preparation of a new generation of derivatized hyaluronic acid from mono-functional vinyl sulfone reagents.

Mono-functional vinyl sulfone reagents have the general formula ($CH_2$=CH—$SO_2$—R) where R is an aryl- or alkyl-group that is preferably but not necessarily hydrophobic. The reaction yielding modification takes place between the reactive vinyl group of the sulfone reagent and the hydroxyl moieties of the hyaluronic acid.

The invention can be used to prepare a wide range of derivatives depending on the nature of the R pendant group. Commercially available compounds on the market include methyl-, ethyl-, phenyl, p-tolyl-, octyl- and other alkyl-/aryl vinyl sulfones.

In contrast to divinyl sulfone (DVS), R-vinyl sulfone reagents are mono-functional thereby avoiding any cross-linking of the HA.

The resulting derivatives, modified with hydrophobic groups, can find application in the cosmetics industry as emulsifiers or in advanced delivery systems, such as, nano-capsules. They can also be used for skin moisturization through film forming. The properties of the derivatives allow the manufacture of new biomaterials while retaining the biocompatibility and biodegradability of the original hyaluronan.

The method is based on a well established chemistry (DVS has been used for more than 20 years to cross-link HA) and it has a number of advantages, being a very versatile method, the HA is used as its sodium salt, it can be done as a "one-pot synthesis", the reaction takes place at room temperature, it is a simple and short process, and the subsequent purification can be done very efficiently with no residue of vinyl sulfone reagents left.

There is a need, particularly in the cosmetics and biomedical industries, for hyaluronic acid based compounds or derivatives that have certain altered characteristics as compared to non-modified HA. Properties of interest are the improved ability to stabilize foam, and the ability to blend with non-hydrophilic materials, such as is used typically in cosmetics products.

The invention provides amphiphilic HA-derivative products with properties of benefit in cosmetics or biomedical applications. These products bind more strongly to the skin so that they are not so easily washed of. The AVS-HA derivatives are also suitable for use in more advanced cosmetic or biomedical formulations, e.g. in the formation of nano/macro capsules or nano/macro spheres for delivery of active compounds or drugs. AVS-HA derivatives of lower molecular weight (MW) will penetrate the skin more efficiently than non-derivatized HA of comparable MW.

Accordingly, in a first aspect the invention relates to a hyaluronic acid derivative comprising n repeating units and having the general structural formula (I):

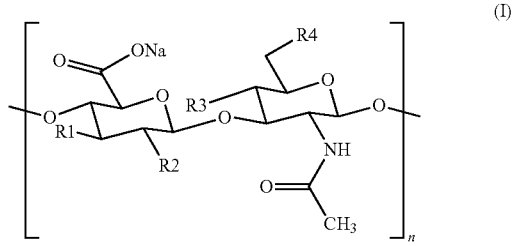

wherein, in at least one repeating unit, one or more of R1, R2, R3, R4 comprises an etherbound aryl/alkyl sulfone having the general structural formula (II), wherein R comprises an alkyl- or aryl-group, and otherwise R1, R2, R3, R4 are hydroxyl groups, OH:

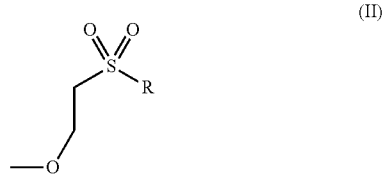

In other words, an aspect of the invention relates to a hyaluronic acid derivative, wherein one or more hydroxyl-group of the hyaluronic acid has been reacted with one or more mono-functional alkyl-/aryl vinyl sulfone compound, to form an ether-bond between the hyaluronic acid and the resulting one or more alkyl-/aryl sulfone compound.

In a second aspect, the invention relates to a hyaluronic acid derivative, wherein an addition reaction has taken place between one or more hydroxyl-group of the hyaluronic acid and one or more mono-functional aryl-/alkyl-vinyl sulfone compounds, to form an ether-bond between the hyaluronic acid and the resulting one or more aryl-/alkyl sulfone compound.

In a third aspect, the invention relates to a process of producing a hyaluronic acid derivative, the process comprising the steps of:
(a) reacting a hyaluronic acid with one or more alkyl-/aryl-vinyl sulfone compounds having the general structural formula (III) under alkaline conditions in an aqueous solution, whereby the hyaluronic acid derivative is formed; and
(b) recovering the hyaluronic acid derivative.

In a fourth aspect, the invention relates to a composition comprising a hyaluronic acid derivative as defined in the first or second aspects, and an active ingredient, preferably the active ingredient is a pharmacologically active agent.

A fifth aspect of the invention relates to a pharmaceutical composition comprising an effective amount of a hyaluronic acid derivative as defined in the first or second aspects, together with a pharmaceutically acceptable carrier, excipient or diluent.

A sixth aspect relates to a pharmaceutical composition comprising an effective amount of a hyaluronic acid derivative as defined in the first or second aspects as a vehicle, together with a pharmacologically active agent.

A seventh aspect relates to a cosmetic article comprising as an active ingredient an effective amount of a hyaluronic acid derivative as defined in the first or second aspects, or a composition as defined in any of the fourth, fifth, or sixth aspects.

In an eighth aspect, the invention relates to a sanitary, medical or surgical article comprising a hyaluronic acid derivative as defined in the first or second aspects, or a composition as defined in any of the fourth, fifth, or sixth aspects, preferably the article is a diaper, a sanitary towel, a surgical sponge, a wound healing sponge, or a part comprised in a band aid or other wound dressing material.

An important aspect relates to a medicament capsule or microcapsule comprising a hyaluronic acid derivative as defined in the first or second aspects, or a composition as defined in any of the fourth, fifth, or sixth aspects.

Final aspects of the invention relate to methods of performing procedures in ophtalmology, in the treatment of osteoarthritis or cancer, hair loss or baldness, of treating a wound, of performing dermal or transdermal administration of a pharmacologically active agent, or dermal administration of a cosmetic, the improvement which comprises the use of a hyaluronic acid derivative as defined in the first or second aspects, or a composition as defined in any of the fourth, fifth, or sixth aspects.

A number of aspects relate to uses of a hyaluronic acid derivative as defined in any of the first or second aspects, or a composition as defined in any of the fourth, fifth, or sixth aspects, for the manufacture of a medicament for the treatment of osteoarthritis, cancer, the manufacture of a medicament for an ophtalmological treatment, the manufacture of a medicament for the treatment of a wound, the manufacture of a medicament for angiogenesis, the manufacture of a medicament for the treatment of hair loss or baldness, or the manufacture of a moisturizer.

BRIEF DESCRIPTION OF DRAWINGS

FIG. 1: $^1$H NMR spectrum (HA, 300 kDa).
FIG. 2: $^1$H NMR spectrum, (PVS-HA from HA 300 kDa) PVS:HA ratio 1.5:1.
FIG. 3: $^1$H NMR spectrum, (PVS-HA from HA 300 kDa) PVS:HA ratio 1.5.
FIG. 4: $^1$H NMR spectrum, (PVS-HA from HA 300 kDa) PVS:HA ratio 10:1

FIG. 5: IR spectrum, (PVS-HA from HA 300 kDa) PVS:HA ratio 10:1.

FIG. 6: $^1$H NMR spectrum, (EVS-HA from HA 300 kDa) EVS:HA ratio 1.5:1.

DETAILED DESCRIPTION OF THE INVENTION

Hyaluronic Acid

"Hyaluronic acid" is defined herein as an unsulphated glycosaminoglycan composed of repeating disaccharide units of N-acetylglucosamine (GlcNAc) and glucuronic acid (GlcUA) linked together by alternating beta-1,4 and beta-1,3 glycosidic bonds. Hyaluronic acid is also known as hyaluronan, hyaluronate, or HA. The terms hyaluronan and hyaluronic acid are used interchangeably herein.

Rooster combs are a significant commercial source for hyaluronan. Microorganisms are an alternative source. U.S. Pat. No. 4,801,539 discloses a fermentation method for preparing hyaluronic acid involving a strain of *Streptococcus zooepidemicus* with reported yields of about 3.6 g of hyaluronic acid per liter. European Patent No. EP0694616 discloses fermentation processes using an improved strain of *Streptococcus zooepidemicus* with reported yields of about 3.5 g of hyaluronic acid per liter. As disclosed in WO 03/054163 (Novozymes), which is incorporated herein in its entirety, hyaluronic acid or salts thereof may be recombinantly produced, e.g., in a Gram-positive *Bacillus* host.

Hyaluronan synthases have been described from vertebrates, bacterial pathogens, and algal viruses (DeAngelis, P. L., 1999, *Cell. Mol. Life. Sci.* 56: 670-682). WO 99/23227 discloses a Group I hyaluronate synthase from *Streptococcus equisimilis*. WO 99/51265 and WO 00/27437 describe a Group II hyaluronate synthase from *Pasturella multocida*. Ferretti et al. disclose the hyaluronan synthase operon of *Streptococcus pyogenes*, which is composed of three genes, hasA, hasB, and hasC, that encode hyaluronate synthase, UDP glucose dehydrogenase, and UDP-glucose pyrophosphorylase, respectively (*Proc. Natl. Acad. Sci. USA.* 98, 4658-4663, 2001). WO 99/51265 describes a nucleic acid segment having a coding region for a *Streptococcus equisimilis* hyaluronan synthase.

Since the hyaluronan of a recombinant *Bacillus* cell is expressed directly to the culture medium, a simple process may be used to isolate the hyaluronan from the culture medium. First, the *Bacillus* cells and cellular debris are physically removed from the culture medium. The culture medium may be diluted first, if desired, to reduce the viscosity of the medium. Many methods are known to those skilled in the art for removing cells from culture medium, such as centrifugation or microfiltration. If desired, the remaining supernatant may then be filtered, such as by ultrafiltration, to concentrate and remove small molecule contaminants from the hyaluronan. Following removal of the cells and cellular debris, a simple precipitation of the hyaluronan from the medium is performed by known mechanisms. Salt, alcohol, or combinations of salt and alcohol may be used to precipitate the hyaluronan from the filtrate. Once reduced to a precipitate, the hyaluronan can be easily isolated from the solution by physical means. The hyaluronan may be dried or concentrated from the filtrate solution by using evaporative techniques known to the art, such as spray drying.

The first aspect of the invention relates to a hyaluronic acid derivative comprising n repeating units and having the general structural formula (I):

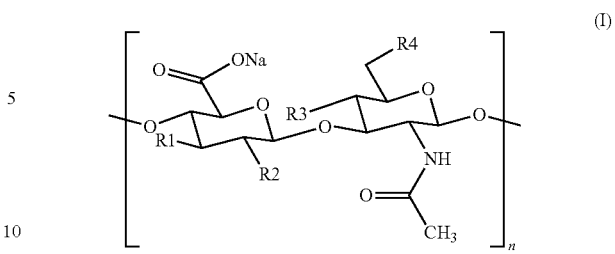

wherein, in at least one repeating unit, one or more of R1, R2, R3, R4 comprises an etherbound aryl/alkyl sulfone having the general structural formula (II), wherein R comprises an alkyl- or aryl-group, and otherwise R1, R2, R3, R4 are hydroxyl groups, OH:

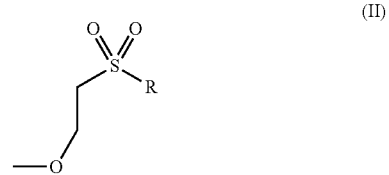

In other words, an aspect of the invention relates to a hyaluronic acid derivative, wherein an addition reaction has taken place between one or more hydroxyl-group of the hyaluronic acid and one or more mono-functional aryl-/alkyl-vinyl sulfone compounds, to form an ether-bond between the hyaluronic acid and the resulting one or more aryl-/alkyl sulfone compound.

A preferred embodiment relates to the hyaluronic acid derivative of the invention, wherein the one or more mono-functional aryl-/alkyl-vinyl sulfone compound has the general structural formula (III), wherein R comprises an alkyl- or aryl-group.

Yet another preferred embodiment relates to the hyaluronic acid derivative of the invention, wherein two or more of R1, R2, R3, R4 comprise one or more etherbound aryl/alkyl sulfone having the general structural formula (II); or wherein three or more of R1, R2, R3, R4 comprise one or more etherbound aryl/alkyl sulfone having the general structural formula (II); or indeed wherein all of R1, R2, R3, R4 comprise one or more etherbound aryl/alkyl sulfone having the general structural formula (II).

The main reaction or addition site in the process of the invention is the primary hydroxyl of the hyaluronic acid repeating unit, also shown as R4 in the structural formula (I).

Accordingly, a preferred embodiment relates to the HA derivative of the invention, wherein at least R4 comprises an etherbound aryl/alkyl sulfone having the general structural formula (II).

Many different alkyl- or aryl-groups are envisioned as being suitable in the mono-functional alkyl-/aryl-vinyl sulfone compounds for use in the present invention.

A preferred embodiment relates to the HA derivative of the invention, wherein R comprises an alkyl-group, preferably the alkyl-group is hydrophobic, preferably the alkyl-group comprises a $C_1$-$C_{20}$ alkyl group, preferably methyl, ethyl, propyl, 2-octenyl, 2-nonenyl, 2-dodecenyl, 2-hexadecenyl, or 2-octadecenyl.

Another preferred embodiment relates to the HA derivative of the invention, wherein R comprises an aryl-group, preferably the aryl-group is hydrophobic, and more preferably the aryl-group is phenyl or p-toluoyl.

Molecular Weight

The level of hyaluronic acid may be determined according to the modified carbazole method (Bitter and Muir, 1962, *Anal Biochem.* 4: 330-334). Moreover, the average molecular weight of the hyaluronic acid may be determined using standard methods in the art, such as those described by Ueno et al., 1988, *Chem. Pharm. Bull.* 36, 4971-4975; Wyatt, 1993, *Anal. Chim. Acta* 272: 1-40; and Wyatt Technologies, 1999, "Light Scattering University DAWN Course Manual" and "DAWN EOS Manual" Wyatt Technology Corporation, Santa Barbara, Calif.

In a preferred embodiment, the hyaluronic acid derivatives obtained by the methods of the present invention have a molecular weight of about 1,000 to about 10,000,000 Da. In a more preferred embodiment, the hyaluronic acid derivatives obtained by the methods of the present invention have a molecular weight of about 5,000 to about 5,000,000 Da. In an even more preferred embodiment, the hyaluronic acid derivatives obtained by the methods of the present invention have a molecular weight of about 10,000 to about 3,000,000 Da.

Another preferred embodiment relates to the product of the first aspect, wherein the hyaluronic acid or salt thereof has a molecular weight in the range of between 300,000 and 3,000,000; preferably in the range of between 400,000 and 2,500,000; more preferably in the range of between 500,000 and 2,000,000; and most preferably in the range of between 600,000 and 1,800,000 Da.

Where recombinantly produced hyaluronic acid or salt thereof is used in the methods of the invention to manufacture the products or compositions of the invention, it may be advantageous for some applications to first reduce the average molecular weight of the hyaluronic acid or derivative or salts thereof. For instance, it has been stated by several manufacturers of so-called low-molecular weight fractions of hyaluronic acid, that it is capable of penetrating the skin barrier to reestablish the natural content of hyaluronic acid in the skin, therefore such fractions are particularly suitable for cosmetic compositions sold as anti-skin-ageing and anti-wrinkle agents. For food applications, low MW hyaluronic acid has been shown to penetrate the gastrointestinal barrier, thereby increasing its bioavailability. Finally, low MW hyaluronic acid exhibits anti-inflammatory effect and have potential applications in the treatment of inflammatory diseases. A reduction of the average molecular weight of a hyaluronic acid or derivative or salt thereof may be achieved by standard methods in the art, such as, simple heat treatment, enzymatic degradation, ultrasound sonication, or acid hydrolysis. See, e.g., U.S. Pat. No. 6,020,484, which describes an ultrasonication technique of HA including NaOCl as additive, and T. Miyazaki et al. (2001) Polymer Degradation and Stability, 74: 77-85.

Accordingly, a preferred embodiment relates to the HA derivative of the invention, wherein the hyaluronic acid or derivative or salt thereof has a low average molecular weight in the range of between 10,000 and 3,000,000 Da; preferably in the range of between 10,000 and 50,000 Da; or preferably in the range of between 50,000 and 500,000 Da; even more preferably in the range of between 80,000 and 300,000 Da.

Degree of Substitution (DS)

DS was determined by $^1$H NMR spectroscopy (10 mg/ml, $D_2O$, 80° C., 128 scans, 400 MHz) according to example 6 below, wherein the peaks from the OSA group were assigned by use of a 2D-NMR (gCOSY). The DS was then calculated by comparing the intensity of the vinyl protons of OSA (5.4 and 5.6 ppm) with that of the acetyl protons (2.0 ppm).

In a preferred embodiment the HA derivative of the first aspect has a Degree of Substitution (DS) in the range of 0.1-100%, preferably 1-90%, more preferably 2-80%, still more preferably 4-70%, even more preferably 8-60%, or 10-50%, 14-40%, 16-30%, or most preferably in the range of 18-25%.

Production

In the methods of the present invention recombinantly produced HA may be used. This sort of HA can be produced by a process, wherein the HA-producing host cells are cultivated in a nutrient medium suitable for production of the hyaluronic acid using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the enzymes involved in hyaluronic acid synthesis to be expressed and the hyaluronic acid to be isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The secreted hyaluronic acid can be recovered directly from the medium.

The resulting hyaluronic acid may be isolated by methods known in the art. For example, the hyaluronic acid may be isolated from the nutrient medium by conventional procedures including, but not limited to, centrifugation, filtration, extraction, spray-drying, evaporation, or precipitation. The isolated hyaluronic acid may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), or extraction (see, e.g., Protein Purification, J.-C. Janson and Lars Ryden, editors, VCH Publishers, New York, 1989).

Host Cells

A preferred embodiment relates to where the hyaluronic acid or salt thereof is recombinantly produced, preferably by a Gram-positive bacterium or host cell, more preferably by a bacterium of the genus *Bacillus*.

The host cell may be any *Bacillus* cell suitable for recombinant production of hyaluronic acid. The *Bacillus* host cell may be a wild-type *Bacillus* cell or a mutant thereof. *Bacillus* cells useful in the practice of the present invention include, but are not limited to, *Bacillus agaraderhens, Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells. Mutant *Bacillus subtilis* cells particularly adapted for recombinant expression are described in WO 98/22598. Non-encapsulating *Bacillus* cells are particularly useful in the present invention.

In a preferred embodiment, the *Bacillus* host cell is a *Bacillus amyloliquefaciens, Bacillus clausii, Bacillus lentus, Bacillus licheniformis, Bacillus stearothermophilus* or *Bacillus subtilis* cell. In a more preferred embodiment, the *Bacillus* cell is a *Bacillus amyloliquefaciens* cell. In another more preferred embodiment, the *Bacillus* cell is a *Bacillus* clausii cell. In another more preferred embodiment, the *Bacillus* cell is a *Bacillus lentus* cell. In another more preferred embodiment, the *Bacillus* cell is a *Bacillus licheniformis* cell. In another more preferred embodiment, the *Bacillus* cell is a *Bacillus subtilis* cell. In a most preferred embodiment, the *Bacillus* host cell is *Bacillus subtilis* A164Δ5 (see U.S. Pat. No. 5,891,701) or *Bacillus subtilis* 168Δ4.

Transformation of the *Bacillus* host cell with a nucleic acid construct of the present invention may, for instance, be effected by protoplast transformation (see, e.g., Chang and Cohen, 1979, Molecular General Genetics 168: 111-115), by using competent cells (see, e.g., Young and Spizizen, 1961, Journal of Bacteriology 81: 823-829, or Dubnau and Davidoff-Abelson, 1971, Journal of Molecular Biology 56: 209-221), by electroporation (see, e.g., Shigekawa and Dower, 1988, Biotechniques 6: 742-751), or by conjugation (see, e.g., Koehler and Thorne, 1987, Journal of Bacteriology 169: 5271-5278).

Process of Derivatization

In a third aspect, the invention relates to a process of producing a hyaluronic acid derivative, the process comprising the steps of:

(a) reacting a hyaluronic acid with one or more alkyl-/aryl-vinyl sulfone compounds having the general structural formula (III) under alkaline conditions in an aqueous solution, whereby the hyaluronic acid derivative is formed; and (b) recovering the hyaluronic acid derivative.

A preferred embodiment relates to the process of the third aspect, wherein the alkyl-/aryl-group, R in (III), comprises an alkyl-group, preferably a hydrophobic alkyl-group, more preferably the alkyl-group comprises a $C_1$-$C_{20}$ alkyl group, and most preferably the alkyl-group comprises a methyl, ethyl, propyl, 2-octenyl, 2-nonenyl, 2-dodecenyl, 2-hexadecenyl, or 2-octadecenyl; or wherein the alkyl-/aryl-group comprises an aryl-group, preferably a hydrophobic aryl-group, and more preferably the aryl-group comprises phenyl or p-toluoyl.

It is also preferred that different mono-functional vinyl sulfone compounds may be employed at the same time, leading to the addition of several different alkyl- or aryl-sulfone compounds to the HA molecule.

Accordingly, a preferred embodiment relates to the process of the third aspect, wherein
the one or more alkyl-/aryl-vinyl sulfone compounds comprise two or more different alkyl- and/or aryl-groups. Preferably, the two or more different alkyl-/aryl-group comprise an alkyl-group, preferably a hydrophobic alkyl-group, more preferably the alkyl-group comprises a $C_1$-$C_{20}$ alkyl group, and most preferably the alkyl-group comprises a methyl, ethyl, propyl, 2-octenyl, 2-nonenyl, 2-dodecenyl, 2-hexadecenyl, or 2-octadecenyl; or the two or more different alkyl-/aryl-group comprise an aryl-group, preferably a hydrophobic aryl-group, and more preferably the aryl-group comprises phenyl or p-toluoyl.

Other Ingredients

In a preferred embodiment, the compositions comprising a HA derivative of the invention may also comprise other ingredients, preferably one or more active ingredient, preferably one or more pharmacologically active substance, and also preferably a water-soluble excipient, such as lactose.

Non-limiting examples of an active ingredient or pharmacologically active substance which may be used in the present invention include protein and/or peptide drugs, such as, human growth hormone, bovine growth hormone, porcine growth hormone, growth hormone releasing hormone/peptide, granulocyte-colony stimulating factor, granulocyte macrophage-colony stimulating factor, macrophage-colony stimulating factor, erythropoietin, bone morphogenic protein, interferon or derivative thereof, insulin or derivative thereof, atriopeptin-III, monoclonal antibody, tumor necrosis factor, macrophage activating factor, interleukin, tumor degenerating factor, insulin-like growth factor, epidermal growth factor, tissue plasminogen activator, factor IIV, factor IIIV, and urokinase.

A water-soluble excipient may be included for the purpose of stabilizing the active ingredient(s), such excipient may include a protein, e.g., albumin or gelatin; an amino acid, such as glycine, alanine, glutamic acid, arginine, lysine and a salt thereof; carbohydrate such as glucose, lactose, xylose, galactose, fructose, maltose, saccharose, dextran, mannitol, sorbitol, trehalose and chondroitin sulphate; an inorganic salt such as phosphate; a surfactant such as TWEEN® (ICI), poly ethylene glycol, and a mixture thereof. The excipient or stabilizer may be used in an amount ranging from 0.001 to 99% by weight of the product.

Several aspects of the invention relate to various compositions and pharmaceuticals comprising, among other constituents, an effective amount of the product as defined in the first aspect, and an active ingredient, preferably the active ingredient is a pharmacologically active agent; a pharmaceutically acceptable carrier, excipient or diluent, preferably a water-soluble excipient, and most preferably lactose.

In addition, aspects of the invention relate to articles comprising a HA derivative as defined in the first aspect or a composition as defined in the aspects and embodiments above, e.g., a cosmetic article, a sanitary article, a medical or surgical article. In a final aspect the invention relates to a medicament capsule or microcapsule comprising a product as defined in the first aspect or a composition as defined in other aspects and embodiments of the invention.

EXAMPLES

Example 1

Phenyl Vinyl Sulfone (PVS) Derivatized Ha (PVS-HA) with PVS:HA Ratio 1.5:1

TABLE 1

| Reagents | MW (Da) | Eq. (—OH) | n (mmol) | m or V (mg or mL) |
|---|---|---|---|---|
| HA | 300 000 | 1 | 0.25 | 100 mg |
| NaOH | 40 | 1 | 0.25 | 1.25 mL |
| PVS | 168 | 1.5 | 0.375 | 63.10 mg |

HA was dissolved in milliQ water (10 mL) overnight at room temperature. NaOH was added to the aqueous HA solution under stirring. PVS was dissolved in acetone (10 mL) and the resulting solution was added drop-wise after 4-5 minutes using a separation funnel. The mixture was stirred overnight at room temperature. The crude mixture was then purified in a dialysis bag (Spectra/Por®, cutoff 14 kDa) immersed in milliQ water (7.5 L). The milliQ water was changed 3 times, after 3 hours, then after one night and finally after 3 hours. The dialysis was monitored by conductivity measurements of the milliQ water and stopped when the conductivity was less than 5 μS/cm. The purified product was finally diluted in milliQ water (50 mL) and freeze-dried.

The reaction yielded a white spongy material of 94.5 mg, partially soluble in milliQ water. The composition of the purified product was analysed by TLC. The values of retention time showed that no residual PVS remained in the purified product. The structure of the purified product was ascertained by 1H NMR and revealed a degree of substitution (DS) of 11% per repeating disaccharide unit (FIG. 2). FT-IR was also used to confirm the formation of phenyl-vinyl sulfone derivatized HA.

A study was conducted on the influence of the amount of PVS involved in the reaction. This study showed that higher amounts of PVS yielded higher degrees of substitution. These were typically between 11% and 55% for PVS:HA ratios ranging from 5:1 to 10:1 (Example 2).

Example 2

Phenyl Vinyl Sulfone (PVS) Derivatized Ha (PVS-HA) with PVS:HA Ratio 5:1 and 10:1

TABLE 2

| Reagents | MW (Da) | Eq. (—OH) | n (mmol) | m or V (mg or mL) |
|---|---|---|---|---|
| HA | 300 000 | 1 | 0.25 | 100 mg |
| NaOH | 40 | 1 | 0.25 | 1.25 mL |
| PVS | 168 | 5 | 1.25 | 210 mg |
| HA | 300 000 | 1 | 0.25 | 100 mg |
| NaOH | 40 | 1 | 0.25 | 1.25 mL |
| PVS | 168 | 10 | 2.50 | 421 mg |

The above derivatives were prepared according to the method described in Example 1. The ratio NaOH:HA was 1:1. The degree of substitution of the derivatives is shown in table 3.

TABLE 3

Degree of substitution of PVS-HA derivatives from PVS:HA ratios 5:1 and 10:1

| PVS:HA | DS |
|---|---|
| 5:1 | 19% |
| 10:1 | 55% |

FIG. 3 and FIG. 4 represent the NMR spectra of the derivatives. FIG. 5 represents an IR spectrum confirming the grafting of PVS on HA chains. Assignment of the bands is presented in table 4.

TABLE 4

Wave number and nature of the additional bands observed on the PVA-HA spectrum compared to the HA spectrum (PVS:HA ratio 10:1).

| Wave number (cm$^{-1}$) | Bond and absorption mode | Comments |
|---|---|---|
| 1600 | C = C ring stretch (1$^{rst}$ absorption) | The 1$^{rst}$ absorption is most probably merged in the band observerd for the C = O stretch (1620 cm$^{-1}$) |

TABLE 4-continued

Wave number and nature of the additional bands observed on the PVA-HA spectrum compared to the HA spectrum (PVS:HA ratio 10:1).

| Wave number (cm$^{-1}$) | Bond and absorption mode | Comments |
|---|---|---|
| 1450 | C = C ring stretch (2$^{nd}$ absorption) | Weak band |
| 1308 | S = O asymmetric stretch | Strong band |
| 1150 | S = O symmetric stretch | This band is already present on the HA spectrum (C-O-C glycoside stretch). Its intensity is clearly increased on the spectrum of the derivative |
| 730 690 | C-H out-of-plane bending | This two-peak pattern is typical of monosubstituted rings |

Example 3

Ethyl Vinyl Sulfone (EVS) Derivatized Ha (EVS-HA) with EVS:HA Ratio 1.5:1

TABLE 5

| Reagents | $M_w$ (Da) | Eq. (—OH,) | n (mmol) | m or V (mg or mL) |
|---|---|---|---|---|
| HA | 300 000 | 1 | 0.25 | 100 mg |
| NaOH | 40 | 1 | 0.25 | 1.25 mL |
| EVS | 120 | 1.5 | 0.375 | 40 μg |

The EVS-HA derivative was prepared according to the method described in Example 1. The reaction yielded a white spongy material, soluble in milliQ water (12.5 g/L). The structure of the purified product was ascertained by $^1$H NMR and revealed a substitution degree of 13.5% per repeating disaccharide unit (FIG. 6). The latter was calculated by comparing the signal of methyl protons on the substituent and that of methyl protons on HA.

The invention claimed is:

1. A hyaluronic acid derivative comprising n repeating units of formula (I):

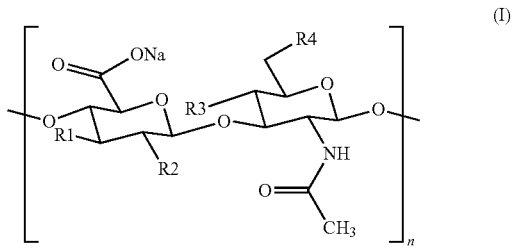

wherein, in at least one repeating unit, one or more of R1, R2, R3, and R4 is an etherbound aryl/alkyl sulfone of formula (II):

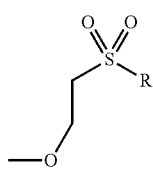

(II)

wherein R is an unsubstituted alkyl-group, a phenyl group, or a p-toluoyl group, and otherwise R1, R2, R3, and R4 are hydroxyl groups, OH.

2. The hyaluronic acid derivative of claim 1, wherein two of R1, R2, R3, and R4 are an etherbound aryl/alkyl sulfone of formula (II).

3. The hyaluronic acid derivative of claim 1, wherein three of R1, R2, R3, and R4 are an etherbound aryl/alkyl sulfone of formula (II).

4. The hyaluronic acid derivative of claim 1, wherein R1, R2, R3, and R4 are an etherbound aryl/alkyl sulfone of formula (II).

5. The hyaluronic acid derivative of claim 1, wherein at least R4 is an etherbound aryl/alkyl sulfone of formula (II).

6. The hyaluronic acid derivative of claim 1, wherein R is an alkyl-group.

7. The hyaluronic acid derivative of claim 6, wherein the alkyl-group is a C1-C20 alkyl group.

8. The process of claim 7, wherein the alkyl-group is methyl, ethyl, or propyl.

9. The process of claim 7, wherein the alkyl-group is 2-octenyl, 2-nonenyl, 2-dodecenyl, 2-hexadecenyl, or 2-octadecenyl.

10. The hyaluronic acid derivative of claim 1, wherein R is a phenyl or p-toluoyl group.

11. The hyaluronic acid derivative of claim 1, which has an average molecular weight of between 10,000 and 3,000,000 Da.

12. A pharmaceutical composition comprising an effective amount of a hyaluronic acid derivative of claim 1 and a pharmaceutically acceptable carrier, excipient or diluent.

13. The composition of claim 12, which also comprises a water-soluble excipient.

14. The composition of claim 13, wherein the water-soluble excipient is lactose.

15. A cosmetic article comprising a hyaluronic acid derivative of claim 1.

16. A sanitary, medical or surgical article comprising a hyaluronic acid derivative of claim 1.

17. A method of treating osteoarthritis, comprising administering an effective amount of a hyaluronic acid derivative of claim 1 to a mammal in need thereof.

18. A method of treating a wound, comprising administering an effective amount of a hyaluronic acid derivative of claim 1 to a mammal in need thereof.

19. A method of treating hair loss or baldness, comprising administering an effective amount of a hyaluronic acid derivative of claim 1 to a mammal in need thereof.

* * * * *